US007435272B2

(12) United States Patent
Aradi et al.

(10) Patent No.: US 7,435,272 B2
(45) Date of Patent: *Oct. 14, 2008

(54) FRICTION MODIFIER ALKOXYAMINE SALTS OF CARBOXYLIC ACIDS AS ADDITIVES FOR FUEL COMPOSITIONS AND METHODS OF USE THEREOF

(75) Inventors: Allen A. Aradi, Richmond, VA (US); Dennis J. Malfer, Glen Allen, VA (US); Scott D. Schwab, Richmond, VA (US); William J. Colucci, Glen Allen, VA (US)

(73) Assignee: Afton Chemical Intangibles, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/421,006

(22) Filed: Apr. 22, 2003

(65) Prior Publication Data

US 2004/0010967 A1    Jan. 22, 2004

Related U.S. Application Data

(63) Continuation-in-part of application No. 10/128,529, filed on Apr. 24, 2002, now Pat. No. 6,866,690.

(51) Int. Cl.
C10L 1/22    (2006.01)
(52) U.S. Cl. .......................................... 44/408; 44/410
(58) Field of Classification Search .................. 44/408, 44/410
See application file for complete search history.

(56) References Cited

U.S. PATENT DOCUMENTS

| | | | |
|---|---|---|---|
| 3,658,707 A | 4/1972 | Delafield | |
| 3,873,278 A * | 3/1975 | Polss .......................... | 44/108 |
| 3,996,024 A | 12/1976 | Coon et al. | |
| 4,086,172 A | 4/1978 | Lowe | |
| 4,129,508 A | 12/1978 | Friihauf | |
| 4,185,594 A | 1/1980 | Perilstein | |
| 4,204,481 A | 5/1980 | Malec | |
| 4,208,190 A | 6/1980 | Malec | |
| 4,211,534 A | 7/1980 | Feldman | |
| 4,231,883 A | 11/1980 | Malec | |
| 4,280,916 A | 7/1981 | Richards et al. | |
| 4,406,803 A | 9/1983 | Liston et al. | |
| 4,409,000 A | 10/1983 | LeSuer | |
| 4,427,562 A | 1/1984 | Horodysky et al. | |
| 4,428,182 A | 1/1984 | Allen et al. | |
| 4,512,903 A | 4/1985 | Schlicht et al. | |
| 4,581,039 A | 4/1986 | Horodysky | |
| 4,589,992 A | 5/1986 | Phillips et al. | |
| 4,617,026 A | 10/1986 | Schaub et al. | |
| 4,729,769 A | 3/1988 | Schlicht et al. | |
| 4,789,493 A | 12/1988 | Horodysky | |
| 4,808,196 A | 2/1989 | Horodysky | |
| 4,836,829 A | 6/1989 | Zimmerman et al. | |
| 4,867,752 A | 9/1989 | Braid et al. | |
| 5,425,789 A | 6/1995 | Lewtas et al. | |
| 5,679,116 A * | 10/1997 | Cunningham et al. ......... | 44/359 |
| 5,858,029 A | 1/1999 | Oumar-Mahamat et al. | |
| 5,968,211 A | 10/1999 | Schilowitz | |
| 6,169,064 B1 | 1/2001 | Krogh et al. | |
| 6,277,158 B1 | 8/2001 | McLean | |
| 6,328,771 B1 | 12/2001 | Moreton | |
| 7,208,022 B2 | 4/2007 | Corkwell et al. | |
| 2002/0095858 A1 | 7/2002 | Krull et al. | |

FOREIGN PATENT DOCUMENTS

| | | | |
|---|---|---|---|
| CA | 2388065 | * | 5/2001 |
| CA | 2352705 | | 5/2002 |
| CN | 2352705 | | 5/1986 |
| DE | 199 55 651 A1 | | 5/2001 |
| EP | 0 482 253 A1 | | 4/1992 |
| EP | 0798364 | | 1/1997 |

(Continued)

OTHER PUBLICATIONS

Derwent Publications Ltd., London, GB; Class E16, AN 1973-30062U; XP002267365 & JP 48 015783 B (Mitsubishi Chemical Inds.).

*Primary Examiner*—Cephia D. Toomer
(74) *Attorney, Agent, or Firm*—Dennis H. Rainear; Paige J. Thomson; J. Clay Matthews

(57) ABSTRACT

A friction modifier for combustible fuels is provided that is prepared by combining a saturated carboxylic acid and an alkoxylated amine or etheramine. Furthermore, there also is an additive concentrate for use in fuels, especially in gasoline for internal combustion engines, comprising (a) a friction modifier comprising of a branched saturated carboxylic acid salt of an alkoxylated amine, such as isohexyloxypropylamine isostearate; (b) a detergent package, as well as the combustible fuels containing this additive concentrate. The particular selection of friction modifier (a) enables a stable additive concentrate to be formulated providing a significant benefit in friction loss when incorporated in gasoline used to fuel an internal combustion engine, and hence an improvement in fuel economy. Moreover, the use of the friction modifier (a) in combination with a detergent package permits increased fuel efficiency to be obtained without increasing the incidence of IVD deposits in combustion engines running on a fuel modified with the additive concentrate.

8 Claims, No Drawings

FOREIGN PATENT DOCUMENTS

| | | |
|---|---|---|
| EP | 0 798 364 A1 | 10/1997 |
| EP | 0 829 527 A1 | 3/1998 |
| EP | 0 869 163 A1 | 10/1998 |
| GB | 767 596 | 2/1957 |
| JP | 62768/78 | 12/1979 |
| JP | 302660/94 | 5/1996 |
| WO | WO 01/72930 A2 | 10/2001 |
| WO | WO 03/068895 A1 | 8/2003 |

* cited by examiner

FRICTION MODIFIER ALKOXYAMINE SALTS OF CARBOXYLIC ACIDS AS ADDITIVES FOR FUEL COMPOSITIONS AND METHODS OF USE THEREOF

This is a Continuation-in-Part patent application claiming priority from the parent patent application with application Ser. No. 10/128,529 filed Apr. 24, 2002 now U.S. Pat. No. 6,866,690.

BACKGROUND OF THE INVENTION

This invention relates to a friction modifier for use in fuels, particularly in gasolines for internal combustion engines. The present invention further relates to new spark-ignition fuel compositions including such a friction modifier and methods for controlling, i.e., reducing or eliminating, deposits and wear in engines, fuel pumps and injectors while imparting enhanced fuel economy performance.

As discussed at some length in U.S. Pat. No. 6,277,158 to McLean, the performance of gasolines and other fuels can be improved through the use of additive technology. For instance, detergents have been used to inhibit the formation of intake system deposits, and thereby improve engine cleanliness and performance. Regulatory mandates have required the introduction of low sulfur fuels, which are known to be less lubricating and raise concerns regarding the durability of fuel pumps and injectors. Sulfur itself is not directly known to be a lubricity modifying agent. However, removal of sulfur by deep hydrotreating is known to also inadvertently remove natural lubricity components of the fuel, such as certain aromatics, carboxylic acids, and esters. Unfortunately, commercial gasoline detergents and dispersants generally show very little friction reducing characteristics until very high concentrations of them are added to the fuel. These high detergent concentrations often reach levels where no-harm effects such as combustion chamber deposits (CCD) become unacceptable.

It has been suggested that separate friction modifiers can be added to gasoline to increase fuel economy by reducing engine friction. Fuel friction modifiers would also serve to protect high-pressure fuel pumps and injectors such as those found in direct injection gasoline (DIG) engines from wear caused by fuel. Worldwide regulations calling for a steep reduction in fuel sulfur levels may exacerbate this wear problem even further. In selecting suitable components for a combined detergent/friction modifier additive package it is important to ensure a balance of detergent and friction modification properties, and so forth. Ideally, the friction modifier should not adversely affect the deposit control function of the detergent. In addition the additive package should not adversely effect on engine performance. For example, the additive package should not promote valve sticking or cause other performance-reducing problems. To be suitable for commercial use, the friction modifier additive also must pass all no-harm testing required for gasoline performance additives. This is often the biggest hurdle for commercial acceptance. The no-harm testing involves 1) compatibility with gasoline and other additives likely to be in gasoline at a range of temperatures, 2) no increase in intake valve deposits (IVD) and CCD, 3) no valve stick at low temperatures, and 4) no corrosion in the fuel system, cylinders, and crankcase. Developing an additive meeting all these criteria is challenging.

Most prior friction modifiers for fuels have been derivatives of natural product (plant and animal derived) fatty acids, with only a few purely synthetic products. For example, WO 01/72930 A2 describes a mechanistic proposal for delivery of a fuel born friction modifier to the upper cylinder wall and into the oil sump resulting in upper cylinder/rings and valves lubrication. The friction modifier is packaged with fuel detergent dispersants such as polyetheramines (PEAs), polyisobutene amines (PIBAs), Mannich bases, and succinimides. Fuel friction modifier prior art identified in the WO '930 reference include U.S. Pat. Nos. 2,252,889, 4,185,594, 4,208,190, 4,204,481, and 4,428,182, which all describe use of fuel modifiers in diesel fuel. Chemistries covered by these patents include fatty acid esters, unsaturated dimerized fatty acids, primary aliphatic amines, fatty acid amides of diethanolamine and long-chain aliphatic monocarboxylic acids. Another specific mentioned patent therein is U.S. Pat. No. 4,427,562, which discloses a lubricant oil and fuel friction modifier made by reacting primary alkoxyalkylamines with carboxylic acids or by aminolysis of the appropriate formate ester, and also U.S. Pat. No. 4,729,769.

U.S. Pat. No. 4,729,769, describes a gasoline carburetor detergent for gasoline compositions derived from reaction products of a $C_6$–$C_{20}$ fatty acid ester, such as coconut oil, and a mono- or di-hydroxy hydrocarbyl amine, such as diethanolamine, as carburetor detergents. The additive in the '769 patent is described as being useful in any gasoline including leaded and those containing methylcyclopentadienyl manganese tricarbonyl (MMT). The fuel described in the '769 patent may contain other necessary additives such as anti-icers, and corrosion inhibitors.

U.S. Pat. No. 5,858,029 describes friction reducing additives for fuels and lubricants involving the reaction products of primary etheramines with hydrocarboxylic acids to give hydroxyamides that exhibit friction reduction in fuels and lubricants. Other prior patents describing friction modifiers include U.S. Pat. No. 4,617,026 (monocarboxylic acid of ester of a trihydric alcohol, glycerol monooleate as fuels and lubricant friction modifier); U.S. Pat. Nos. 4,789,493, 4,808,196, and 4,867,752 (use of fatty acid formamides); U.S. Pat. No. 4,280,916 (use of fatty acid amides); U.S. Pat. No. 4,406,803 (use of alkane 1,2-diols in lubricants to improve fuel economy); and U.S. Pat. No. 4,512,903 (use of amides from mono- or polyhydroxy substituted aliphatic monocarboxylic acids and amines). U.S. Pat. No. 6,328,771 discloses fuel compositions containing lubricity enhancing salt compositions made by the reaction of certain carboxylic acids with a component that is comprised of a heterocyclic aromatic amine. EP 0 798 364 discloses diesel fuel additives comprising a salt of a carboxylic acid and an aliphatic amine, or an amide obtained by dehydration-condensation between a carboxylic acid and an aliphatic amine.

EP 0 869 163 A1 describes a method for reducing engine friction by use of ethoxylated amines. In addition, U.S. Pat. No. 4,086,172 (oil soluble hydroxyamines such as "ETHOMEEN 18-12™" formula $C_{18}H_{37}N$—$(CH_2CH_2OH)_2$ as lubricant antioxidant); U.S. Pat. No. 4,129,508 (reaction products of succinic acid or anhydride and a polyalkylene glycol or monoether, an organic basic metal, and an alkoxylated amine as a demulsifier); U.S. Pat. Nos. 4,231,883; 4,409,000; and 4,836,829, all teach various uses of hydroxyamines in fuels and lubricants.

U.S. Pat. No. 6,277,158 describes the current practice in the supply of gasoline as generally being to pre-mix the fuel additives into a concentrate in a hydrocarbon solvent base, and then to inject the concentrate into gasoline pipelines used to fill tankers prior to delivery to the customer. To facilitate injection of the concentrate into the gasoline, it is important that the concentrate is in the form of a low viscosity, homogeneous liquid.

Copending U.S. patent application Ser. No. 10/128,529 is the parent of the present application and is directed to the use of saturated branched carboxylic acid salts of alkylated amines for friction modification of fuel.

A friction modifier may be added to the gasoline as the lone additive or in combination with a detergent dispersant package that is fully formulated for fuel compatibility at conditions likely to be experienced by the engine. In addition, a need may exist for a detergent/friction modifier additive concentrate for gasoline that provides all of fuel economy enhancement, deposit control and friction reduction. In addition it should be stable over the temperature range at which the concentrate may feasibly be stored, and which does not adversely affect the performance and properties of the finished gasoline or engine in which the gasoline is used, and in particular, does not lead to increased IVD problems.

SUMMARY OF THE INVENTION

The present invention provides a friction modifier prepared by combining saturated carboxylic acid and an alkoxylated amine or etheramine. The present invention also relates to a composition of matter useful as an additive concentrate for combustion engine fuels containing the friction modifier and a detergent package. In one embodiment, there is a composition of matter useful as an additive concentrate for combustion engine fuels, containing (a) a friction modifier comprising branched or linear saturated carboxylic acid salt of an alkoxylated or ether amine, and (b) a detergent package.

As used herein, the term "alkoxylated" or "alkoxy" is generic in that it can mean monoalkoxylated, or polyalkoxylated (such as "dialkoxylated"). The term "amine," as used in connection with the friction modifier (a), is generic in that it can mean ammonia, a monoamine, or polyamine (such as "diamine").

In one preferred aspect, the friction modifier (a) comprises branched or linear saturated carboxylic acid salt of a mono- or di-alkoxylated amine. In another preferred aspect, the friction modifier (a) comprises an alkoxyamine isostearate or etheramine isostearate. It also will be appreciated that the friction modifier (a) and detergent package (b) are not necessarily identical materials.

As used herein, the terms "alkoxylated amine" and "etheramine" mean a primary, secondary or tertiary amine that has at least (a) one —OR alkoxy group, where R is an aliphatic hydrocarbon of $C_1$–$C_{28}$, or (b) one R—O—R' ether group where R and R' are independently aliphatic hydrocarbons of $C_1$–$C_{28}$.

When incorporated into an engine fuel, the friction modifier (a) is included in an amount effective such that the engine running on the fuel has significantly reduced engine friction loss, which translates into increased fuel economy, without having a deleterious affect on engine or valve deposits. This can be accomplished in this particular case by the use of a saturated branched or linear carboxylic acid as the starting material. Unsaturated materials can cause problems since they contribute to deposits in the engine.

In one particular aspect, the present invention provides an additive concentrate for use in combustion engine fuels comprising, by weight based on the total weight of the concentrate:

(a) 0.2 to 50% friction modifier comprising of a branched or linear saturated carboxylic acid salt of a mono- or dialkoxy amine or etheramine, which preferably is a liquid or can be solubilized at room temperature and pressure;

(b) 40 to 99.8% detergent package mainly comprised of a detergent and carrier mix; and (c) 0 to 80% solvent.

In one example of the invention, the friction modifier is an etheramine isostearate or a branched or linear saturated isomer thereof, or mixtures thereof. Also, the friction modifier (a) can be ashless or ash-producing, and in a preferred embodiment is ashless.

In one aspect, the particular selection of a branched or linear saturated carboxylic acid salt of an alkoxy or ether amine, in combination with a detergent package, enables a stable additive concentrate to be formulated having a friction modifier effective to achieve a significant benefit in friction loss, and hence an improvement in fuel economy, yet without leading to an increase in IVD.

In one preferred embodiment, the friction modifier as defined herein comprises a mixture of different alkoxy monoamine salts having different respective fatty acid moieties with different length backbones and variable degrees of branching. Such mixtures of friction modifier species can further lower the melting point of that additive ingredient, providing a friction modifying component more prone to be a liquid. The preferred friction modifier is typically a liquid over at least the temperature range of about −20° C. to about +35° C.

It has been found that the friction modifier comprising a branched saturated carboxylic acid salt of an alkoxy or ether amine provides all the benefits explained above, while comparison unsaturated compounds such as n-butylamine oleate in particular, when used in combination with a detergent, undesirably lead to increases in the incidence of IVD. While not desiring to be bound to a theory, it nonetheless is postulated that provision of a saturated fatty acid moiety in the friction modifier compound in accordance with the present invention helps in not interfering with the desired IVD control mechanisms sought when using fuels modified with the additive concentrate containing the friction modifier and detergent, while imparting the separately desired friction modification functionality.

In one embodiment, the provision of structural branching in the polyalkylene backbone of the fatty acid moiety of a branched saturated carboxylic acid salt of an alkoxy or ether amine used as the friction modifier in the practice of the present invention has been found to increase the likelihood that the saturated friction modifier additive compound remains fluid and easily miscible with fuels at normal operating temperatures. However, solubilizing agents, for example hydrocarbon solvents, such as alcohols or organic acids, may be included if desired or needed to help solubilize a solid form of a friction modifier, and therefore are not excluded from the scope of the present invention, although the solubilizing agents are not an essential requirement.

Further, this invention is also directed to methods of increasing fuel efficiency while controlling deposits in gasoline engines. In another embodiment, the inventive composition of matter is provided as an aftermarket or "top treat" fuel additive composition.

DETAILED DESCRIPTION OF THE PREFERRED EMBODIMENTS

The present invention is directed in an embodiment to friction modifier prepared by the reaction, mixing or combination of a saturated fatty acid and an alkoxylated amine or etheramine. In one exemplary aspect, the friction modifier is prepared by the reaction, mixing or combination of (i) a branched saturated fatty acid, and (ii) a monoalkoxy monoamine, or a polyalkoxy (i.e., polyether) monoamine, or a monoalkoxy polyamine, or a polyalkoxypolyamine, or a combination thereof. In one preferred aspect, the branched saturated fatty acid used in the preparation of the friction modifier is a $C_6$ to $C_{28}$ branched saturated fatty acid.

When this friction modifier is used in combination with a detergent package for fuels combusted in engines having intake valves, a remarkable performance enhancement effect is provided combining fuel economy improvements without increasing IVD. For instance, saturated and branched carboxylic acid salts of an alkoxy monoamine are friction modifiers found by the present investigators to show especially excellent gasoline fuel economy enhancing properties through, for example, 1) the lowering of the boundary friction coefficient of the thin lubricating oil film on the upper cylinder walls of the engine, and 2) the lowering of IVD when used in combination with a detergent or deposit inhibitor to levels lower than those of the deposit inhibitor alone. They also may exhibit superior demulse capabilities.

Friction Modifier

The friction modifier used in the present invention, in a preferred embodiment, comprises a branched or linear saturated carboxylic acid salt of a monoalkoxylated or polyalkoxylated amine. In a more preferred embodiment, branching is included in the backbone of the saturated carboxylic acid to enhance compatibility with fuels at low ambient temperatures.

A non-limiting structural representation of a suitable branched saturated carboxylic acid salt of an alkoxy amine is the following general structural formula I:

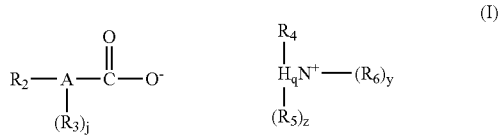

where $R_2$ and $R_3$ each independently represents an alkyl group, preferably a $C_1$–$C_6$ alkyl group, and more preferably methyl; j is 1 to 20, preferably 1 to 5; A represents —$(CH_2)_x$— where x is 4 to 20; with the provisos that each $R_3$ is substituted for a hydrogen of a backbone carbon atom in A and no more than two $R_3$ groups are bonded to any given one backbone carbon atom in A; $R_4$, $R_5$ and $R_6$ each independently represents a hydrocarbyl group, such as an alkyl or alkoxy group, or a hydrogen atom; and q is 1, 2 or 3, and z and y each independently is 0 or 1, with the proviso that q is 3 where z and y each is 0, q is 2 when one of z or y is 1 and the other is 0, and q is 1 when z and y each is 1, with the further proviso that at least one of $R_4$, $R_5$ or $R_6$ is a hydrocarbyl group containing at least one alkoxy group or at least one ether group.

In one further embodiment, $R_4$ and $R_5$ in structure I each independently represent an aliphatic $C_1$–$C_8$ alkyl group, which can be straight, branched, nonsubstituted, or substituted, and with the proviso that any branching or substitution(s) present does not undermine the friction modifying functionality of the ingredient or render it incompatible with the modified fuel composition and the further proviso that if $R_4$ and $R_5$ do not contain an ether bond, then $R_6$ does contain an ether bond. In one particular embodiment, $R_4$ and $R_5$ each independently represents a nonhydroxylated, aliphatic $C_1$–$C_8$ alkyl group, and $R_6$ has an ether bond. In a further aspect, $R_2$ and $R_3$ in structure I each can independently represent an aliphatic $C_1$–$C_6$ alkyl group, which can be straight, branched, cyclic, nonsubstituted, or substituted, and with the proviso that any branching or substitution(s) present does not undermine the friction modifying functionality of the ingredient or render it incompatible with the modified fuel composition. At least one of $R_4$, $R_5$ or $R_6$ must have at least one alkoxy group or an ether linkage.

The branched saturated carboxylic acid salt of an alkoxy amine used as friction modifiers in this invention can be made, for example, by mixing (i) a branched saturated carboxylic acid, or mixtures thereof, with (ii) a mono- and/or di-alkoxy monoamine, and/or a mono- and/or polyalkoxylated polyamine, at an approximately 1:1 molar ratio, and with stirring at temperatures ranging from 25° C. to 75° C., until there is no further temperature change.

Mixtures of friction modifiers as defined herein having different back bone lengths and variable degrees of branching can be advantageously used as the friction modifier component (a). Such mixtures can further lower the melting point of the additive ingredient, providing a friction modifying component more prone to be in a liquid state.

The carboxylic acids useful in the present invention can include but are not limited to branched or linear saturated carboxylic acids.

More specifically, the carboxylic acids useful herein can include, but are not limited to, isostearic, 2-ethyl hexanoic, lauric, palmitic, stearic, decanoic, dodecanoic, undecanoic, myristic, capric, caproic, caprylic, methylvaleric, dimethylvaleric, and isomers and mixtures thereof.

In addition, other carboxylic acids useful herein can be alkyl acids in which the alkyl group is cyclic, referred to herein as cyclic carboxylic acids.

In addition, the carboxylic acid used in the present invention can be a monocarboxylic acid, a dicarboxylic acid, a polycarboxylic acid, or a mixture thereof.

The alkoxylated amine moiety of the friction modifier compound of structure I can be, for example, a monoalkoxy or monoether monoamine moiety, such as an isopropyloxypropyl amine moiety, or, alternatively, a dialkoxy monoamine moiety. Alternatively alkoxy polyether amines, such as alkoxy diamines are useful herein.

As an exemplary friction modifier component (a), there is the amine salt prepared by combining isodecyloxypropylamine or a homologue thereof with isostearic acid.

The salt resulting from combining lauric acid and isopropyloxypropylamine can be used as the friction modifier as well as saturated branched isomers thereof. An exemplary non-limiting structural representation of an alkoxyamine isostearate is the following structure II:

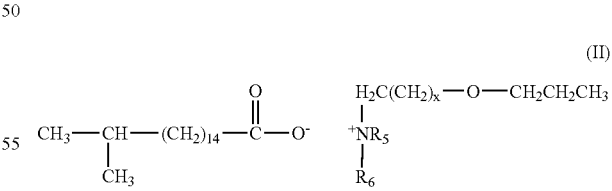

Another example of the salt of the present invention can be made by mixing 2-ethylhexyloxypropylamine and isostearic acid at a 1:1 molar ratio, and stirring at temperatures ranging from 25° C. to 75° C. until there is no further temperature change.

The treat level of the friction modifier of the present invention in the finished gasoline generally will be an amount providing the improved performance effects, such as in terms of improving fuel efficiency, and so forth, as described herein.

For example, a treat level of at least about 5 PTB (pounds per thousand barrels), and more preferably at least about 50 PTB, of the present friction modifier can be used for gasolines.

The friction modifier component (a) can be used as a relatively pure form of linear or branched saturated carboxylic acid salts of an alkoxy amine, or optionally in the co-presence of other linear or branched carboxylic acid salts of alkylated amines or alkoxy amines having an iodine number less than 10, as long as the latter do not adversely affect the desired performance characteristics of this additive, as identified herein.

Nonlimiting examples of alkoxy amines or ether amines useful in the present invention for combining with the branched or linear saturated carboxylic acids include: primary ether amines, ether diamines, precursors thereof, derivatives thereof, and mixtures thereof More specifically, these can include but are not limited to one or more of:

Isohexyloxypropylamine
2-ethylhexyloxypropylamine
Octyl/Decyloxypropylamine
Isodecyloxypropylamine
Isododecyloxypropylamine
Isotridecyloxypropylamine
$C_{12-15}$ alkyloxypropylamine
Isodecyloxypropyl-1,3-diaminopropane
Isododecyloxypropyl-1,3-diaminopropane
Isotridecyloxypropyl-1,3-diaminopropane
Isohexyloxypropylamine
2-ethylhexyloxypropylamine
Octyl/Decyloxypropylamine
Isodecyloxypropylamine
Isopropyloxypropylamine
Tetradecyloxypropylamine
Dodecyl/tetradecyloxypropylamine
Tetradecyl/dodecyloxypropylamine
Octadecyl/hexadecyloxypropylamine Many ether monoamines useful in preparing the friction modifier salts of the present invention are commercially available from Tomah[3] Products, Inc., Milton, Wis.

A preferred etheramine herein is isodecyloxypropylamine.

Also useful in preparing the friction modifier salts of the present invention are ether diamines, such as but not limited to tetradecyloxypropyl-1,3-diaminopropane, and $C_{12}$–$C_{15}$ alkyloxypropyl-1,3-diaminopropane.

Gasoline Performance Additive (GPA) Package

A traditional GPA package is generally comprised of a detergent package that mainly comprises a detergent and a carrier mix whose primary purpose is to keep the components parts of the engine free of deposits. Other components present in the GPA package typically include a corrosion inhibitor, a demulsifying agent, antioxidants and solvents. In some cases a marker is added to the GPA package for identification. Thus, the detergent package typically is introduced to the fuel additive concentrate as part of a GPA package, although this is not required.

Detergent (Deposit Inhibitor) Package

The detergent or deposit inhibitor used in the detergent package component of the additive concentrate described herein may include any suitable commercially available detergent or deposit inhibitor available for this function. Deposit inhibitors for gasoline, usually referred to as detergents or dispersants, are well known and a variety of compounds can be used. Examples include Mannich bases, polyalkylene amines, and polyalkylene succinimides where the polyalkylene group typically has a number average molecular weight of from 600 to 2000, preferably from 800 to 1400, and polyether amines. A preferred detergent for the additive concentrate of the present invention is a Mannich base detergent.

The Mannich base detergents suitable for use in the present invention include the reaction products of a high molecular weight alkyl-substituted hydroxyaromatic compound, aldehydes and amines. The alkyl-substituted hydroxyaromatic compound, aldehydes and amines used in making the Mannich reaction products of the present invention may be any such compounds known and applied in the art.

Suitable Mannich detergents for use in the present invention include those detergents taught in U.S. Pat. Nos. 4,231, 759; 5,514,190; 5,634,951; 5,697,988; 5,725,612; and 5,876, 468, the disclosures of which are incorporated herein by reference. Suitable Mannich base detergents also include, for example, HiTEC® 4995 and HiTEC® 6410 Detergents and are available from the Ethyl Corporation, Richmond, Va., U.S.A.

Carrier

In a preferred embodiment, the detergents are preferably used with a carrier or induction aid. This carrier typically will be a carrier fluid. Such carriers can be of various types, such as, for example, liquid poly-a-olefin oligomers, mineral oils, liquid poly(oxyalkylene) compounds, polyalkenes, and similar liquid carriers. Mixtures of two or more such carriers can also be employed.

Optional Solvent Among other things, the kinematic viscosity of the additive concentrate can be adjusted (reduced) by solvent addition, if desired or needed. To achieve this, a solvent can be added to the concentrate, such as an aromatic hydrocarbon solvent or an alcohol. Examples include toluene, xylene, tetrahydrofuran, isopropanol isobutylcarbinol, n-butanol, and petroleum hydrocarbon solvents such as solvent naphtha, and the like.

Fuel Compositions

The fuel compositions of the present invention may contain supplemental additives in addition to deposit control additives described above. Said supplemental additives include dispersants/detergents, antioxidants, carrier fluids, metal deactivators, dyes, markers, corrosion inhibitors, biocides, antistatic additives, drag reducing agents, demulsifiers, emulsifiers, dehazers, anti-icing additives, octane enhancers, anti-knock additives, anti-valve-seat recession additives, lubricity additives, surfactants and combustion improvers. A particularly preferred supplemental additive is methyl cyclopentadienyl manganese tricarbonyl (MMT).

In another aspect, the present invention provides a fuel composition comprising combustible fuel and from 50 to 2500 ppm by weight of an additive combination comprising components (a), (b), and optionally a solvent (c), as described herein.

The combustible fuel used in the fuel composition of this invention is generally a petroleum hydrocarbon useful as a fuel, e.g., gasoline, for internal combustion engines. Such fuels typically comprise mixtures of hydrocarbons of various types, including straight and branched chain paraffins, olefins, aromatics and naphthenic hydrocarbons, and other liquid hydrocarbonaceous materials suitable for spark ignition gasoline engines.

These compositions are provided in a number of grades, such as unleaded and leaded gasoline, and are typically derived from petroleum crude oil by conventional refining and blending processes such as straight run distillation, thermal cracking, hydrocracking, catalytic cracking and various reforming processes. Gasoline may be defined as a mixture of liquid hydrocarbons or hydrocarbon-oxygenates having an initial boiling point in the range of about 20 to 60° C. and a final boiling point in the range of about 150 to 230° C., as determined by the ASTM D86 distillation method. The gasoline may contain other combustibles such as alcohol, for example methanol or ethanol.

The combustible fuels used in formulating the fuel compositions of the present invention preferably include any combustible fuels suitable for use in the operation of direct injection gasoline engines such as leaded or unleaded motor gasolines, and so-called reformulated gasolines which typically contain both hydrocarbons of the gasoline boiling range and fuel-soluble oxygenated blending agents ("oxygenates"), such as alcohols, ethers and other suitable oxygen-containing organic compounds. Preferably, the fuel is a mixture of hydrocarbons boiling in the gasoline boiling range. This fuel may consist of straight chain or branch chain paraffins, cycloparaffins, olefins, aromatic hydrocarbons or any mixture of these. The gasoline can be derived from straight run naptha, polymer gasoline, natural gasoline or from catalytically reformed stocks boiling in the range from about 80° to about 450° F. The octane level of the gasoline is not critical and any conventional gasoline may be employed in the practice of this invention.

Oxygenates suitable for use in the present invention include methanol, ethanol, isopropanol, t-butanol, mixed $C_1$ to $C_5$ alcohols, methyl tertiary butyl ether, tertiary amyl methyl ether, ethyl tertiary butyl ether and mixed ethers. Oxygenates, when used, will normally be present in the base fuel in an amount below about 30% by volume, and preferably in an amount that provides an oxygen content in the overall fuel in the range of about 0.5 to about 5 percent by volume.

The additives used in formulating the preferred fuels of the present invention can be blended into the base fuel individually or in various sub-combinations.

The friction modifier additive according to the present invention can be used generally in internal combustion engines that burn liquid fuel, especially spark-ignited gasoline engines that are carbureted, port-fuel injected (PFI), and direct injected gasoline (DIG). A preferred embodiment of the present invention comprises a method for increasing fuel efficiency while controlling engine deposit and fuel systems wear. This is achieved by introducing into the engine fuel composition a) a spark-ignition fuel and b) a deposit inhibitor package/friction modifier additive as described herein which has been dispersed therein.

A very significant feature of the present invention is the improved compatibility of the fuel additive package which is achieved because the alkoxyamine salt of the carboxylic acid is a liquid at room temperature. The salt therefore easily dissolves in the GPA, disperses better than the prior art solid salts, and the package exhibits much better low-temperature compatibility and solubility.

Another important feature of an embodiment of the present invention is the marked reduction in acid content from alkoxyamine salts of the carboxylic acids compared to the acid content from the alkylamine salts of the carboxylic acids, without a sacrifice in either friction modification or fuel economy increase. The reduced acid content is important for, among others, reducing corrosion in the engine and fuel delivery system. Thus the n-butylamine salt of the oleate has an acid content of 79.65% and the n-butylamine salt of the Century 1101 mixed acids has 80.92% acid content. However, the inventive material comprising the alkoxyamine (PA 14) salt of the Century 1101 mixed acids has an acid content of only 56.75%, a dramatic reduction in acidity. This translates to reduced corrosion in the engine, without loss of friction modification or reduced fuel economy.

EXAMPLES

The practice and advantages of this invention are demonstrated by the following examples, which are presented for purposes of illustration and not limitation.

Test Samples Preparation

For purposes of the following examples, a number of different friction modifiers were tested either as a 5% solution in a 5W30 GF-3 test oil for boundary friction measurements, or in combination with the detergent HiTEC® 6421 for Sequence VI-B fuel economy engine tests and IVD measurements. HiTEC® 6421 Gasoline Performance Additive (GPA) is commercially available from Ethyl Corporation, Richmond, Va., U.S.A. For the Sequence VI-B engine fuel economy testing described in the examples below, the friction modifier/GPA combinations were formulated to contain (a) 50 PTB friction modifier, and (b) 80.9 PTB of HiTEC® 6421 GPA as the detergent source.

An example of a friction modifier (FM) additive representing the present invention is the salt formed by combining a saturated branched carboxylic acid Century 1101 (Arizona Chemical) with isodecyloxypropylamine (FM-1). As a comparison, n-butylamine oleate (FM-2) instead was used in the same wt % proportion in place of FM-1 to demonstrate the IVD control superiority of the invention FM-1. Another friction modifier prepared for testing in an example below, and representing the present invention, contained friction modifier FM-3 made by reacting n-butyl amine and a mixture of branched saturated fatty acids. The mixture of branched saturated fatty acids was obtained from Arizona Chemical under the generic product name Century 1101. A reaction product of coconut oil and diethanolamine (FM-4) made according to the method described in U.S. Pat. No. 4,729,769, was also used as a comparative friction modifier in several of the examples below.

Sequence VI-B fuel economy increase (FEI) values were determined for additive formulations containing 80.9 PTB of the Mannich Detergent Package A (i.e., HiTEC® 6421 GPA) at a regular treat level top treated with 50 PTB friction modifier isodecyloxypropyl amine salt of branched saturated fatty acid (FM-1), and, separately, with a friction modifier FM-4, made by reacting coconut oil and diethanolamine. A third friction modifier prepared for testing as above contained the friction modifier FM-3 made by reacting n-butyl amine and a mixture of branched saturated fatty acids obtained from Arizona Chemical under the generic product name Century 1101. The mixture of n-butyl amine and fatty acids was mixed in a 1:1 molar ratio with stirring at temperatures ranging from 25° C. to 75° C. until there is no further temperature change.

To obtain the fuel economy increase (FEI) data for each friction modifier additive described in Table 2 below, a Sequence VI-B engine was first calibrated with a standard baseline calibration oil (BC oil). The oil used to test the friction modifier additives was an SAE Grade 5W30 oil of GF-3 quality with HiTEC® 7133 lubricant friction modifier, which was used so that the results obtained would reflect real world performance of the candidate gasoline additives in commercial motor oils. The test was run according to standard Sequence VI-B procedure. The engine was run on additive free base fuel for 80 hours to age the oil, and then the brake specific fuel consumption (BSFC) measured for all five Sequence VI-B stages. Then the fuel was switched to that containing the detergent/friction modifier additive formulation, and the engine allowed to equilibrate before a second BSFC was measured. The fuel was switched back to base fuel, the engine allowed to equilibrate, and a third BSFC was measured. Finally, the friction modifier was injected into the sump in an amount to simulate long-term accumulation in the oil, and a final BSFC measured. The FEI baseline for the fuel itself is 1.52. From this data instantaneous and long-term fuel economy increase (FEI) was calculated for each respective additive. Example values are shown in the Table 1 below.

TABLE 1

| Additive Formulation | Instantaneous FEI (%) | Long Term FEI (%) |
|---|---|---|
| Mannich Detergent Package (A) + FM-1 (inventive) | 2.04 | 2.24 |
| Mannich Detergent Package (A) + FM-3 (non-inventive) | 1.99 | 2.45 |
| Mannich Detergent Package (A) + FM-4 (non-inventive) | 1.73 | 2.05 |

These results clearly demonstrate no detriment in fuel economy with use of the additive FM-1 according to the invention versus the comparison additives (i.e., FM-3 and FM-4). Furthermore, the acid content of the additized fuel of the invention is dramatically reduced relative to the acid content of the fuels additized with FM-3 or FM-4.

Example 2

IVD measurements were carried out on a Ford 2.3 L engine according to a modified version of the ASTM D-6201 procedures to compare the inventive FM-1 and conventional FM-2 additives. These IVD measurements differed from ASTM D-6021 only in that the valves were used only once with each test and then were replaced with new ones before any subsequent test; otherwise the protocols were the same. IVD levels of fuels containing 80.9 PTB of the Mannich detergent (and carrier fluid) supplied as HiTEC® 6421 GPA, with 50 PTB friction modifier isodecyloxypropylamine salt of Century 1101 fatty acid (FM-1), and, separately, with 50 PTB n-butylamine oleate (FM-2), were measured. The results are summarized in Table 2.

TABLE 2

| Additive Formulation | Intake Valve Deposit (IVD) in mg |
|---|---|
| Mannich Detergent (A) | 209.8 |
| (A) + FM-1 (inventive) | 204.6 |
| (A) + FM-2 (non-inventive) | 285.3 |

The results are also illustrated in Table 3, which shows the significantly better IVD control and reduction achieved with the fuel composition containing the inventive alkoxyamine salt of a branched saturated fatty acid friction modifier (FM-1) and detergent combination, as compared to the comparison fuel composition containing the n-butylamine oleate additive (FM-2) combined with the same type of detergent.

The data indicate that both alkoxyamine salts of branched saturated fatty acids and n-butylamine oleate function as friction modifiers for gasoline, but that the use of fuel additives containing both a detergent and the inventive salt results in significantly decreased occurrence of IVD, while the use of fuel additives containing the detergent in combination with n-butylamine oleate results in an undesirable increase in the occurrence of IVD.

It is to be understood that the reactants and components referred to by chemical name anywhere in the specification or claims hereof, whether referred to in the singular or plural, are identified as they exist prior to coming into contact with another substance referred to by chemical name or chemical type (e.g., base fuel, solvent, etc.). It matters not what chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together either in performing a desired chemical reaction (such as a Mannich condensation reaction) or in forming a desired composition (such as an additive concentrate or additized fuel blend). It will also be recognized that the additive components can be added or blended into or with the base fuels individually per se and/or as components used in forming preformed additive combinations and/or sub-combinations. Accordingly, even though the claims hereinafter may refer to substances, components and/ or ingredients in the present tense ("comprises", "is", etc.), the reference is to the substance, components or ingredient as it existed at the time just before it was first blended or mixed with one or more other substances, components and/or ingredients in accordance with the present disclosure. The fact that the substance, components or ingredient may have lost its original identity through a chemical reaction or transformation during the course of such blending or mixing operations is thus wholly immaterial for an accurate understanding and appreciation of this disclosure and the claims thereof.

As used herein the term "fuel-soluble" or "gasoline-soluble" means that the substance under discussion should be sufficiently soluble at 20° C. in the base fuel selected for use to reach at least the minimum concentration required to enable the substance to serve its intended function. Preferably, the substance will have a substantially greater solubility in the base fuel than this. However, the substance need not completely dissolve in the base fuel in all proportions.

At numerous places throughout this specification, reference has been made to a number of patents and patent applications. All such cited documents are expressly incorporated in full into this disclosure as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A composition of matter useful as an additive concentrate for combustion engine fuels, comprising a saturated branched or cyclic carboxylic acid salt of isodecyloxypropylamine and a detergent package comprising detergent and carrier fluid.

2. The composition of claim 1, wherein the carboxylic acid is selected from the group consisting of monocarboxylic acids, dicarboxylic acids, and polycarboxylic acids.

3. The composition of claim 1, wherein the detergent of the detergent package is selected from the group consisting of Mannich bases, polyalkylene amines, polyalkylene succinimides polyether amines, singly or in combinations thereof.

4. The composition of claim 1, further comprising a petroleum solvent.

5. A composition of matter useful as an additive concentrate for combustion engine fuels, comprising the reaction product from combining isodecyloxyproplymine and isostearic acid, and a detergent package comprising detergent and carrier fluid.

6. A method for increasing the fuel efficiency in a gasoline combustion engine, said method comprising combusting in the engine a gasoline fuel comprising a major amount of a fuel boiling in the gasoline boiling range, and a minor amount of a branched or cyclic saturated carboxylic acid salt of an alkoxylated amine or etheramine, wherein the amine is selected from the group consisting of Isododecyloxypropylamine
Isotridecyloxypropylamine
$C_{12-15}$ alkyloxypropylamine
Isodecyloxypropyl-1,3-diaminopropane
Isododecyloxypropyl-1,3-diaminopropane
Isotridecyloxypropyl-3-diaminopropane
Isohexyloxypropylamine
2-ethylhexyloxypropylamine
Octyl/Decyloxypropylamine
Isodecyloxypropylamine
Isopropyloxypropylamine
Tetradecyloxypropylamine
Dodecyl/tetradecyloxypropylamine
Tetradecyl/dodecyloxypropylamine
Octadecyl/hexadecyloxypropylamine
Tetradecyloxypropyl-1,3-diaminopropane, and
$C_{12}$–$C_{15}$ alkyloxypropyl-1,3-diaminopropane.

7. The method of claim 6, wherein the saturated carboxylic acid salt of an alkoxylated amine or etheramine is present in the fuel in an amount sufficient to increase the fuel efficiency relative to the fuel efficiency obtained by combusting in said engine a gasoline fuel which does not comprise a saturated carboxylic acid salt of an alkoxylated amine or etheramine.

8. The method of claim 6, wherein the engine has intake valves and the fuel further comprises a minor amount of a detergent in an amount sufficient to reduce the amount of intake valve deposits (IVD) formed relative to the amount of intake valve deposits formed by combusting in said engine a gasoline fuel which comprises in equivalent amount a friction modifier formed by combining a branched or cyclic saturated carboxylic acid and an alkoxylated amine or etheramine.

* * * * *